United States Patent
Jorda et al.

(10) Patent No.: US 11,648,569 B2
(45) Date of Patent: May 16, 2023

(54) USE OF ALKOXYLATED AMINES AS COLLECTOR AGENTS FOR ORE BENEFICIATION

(71) Applicant: ARKEMA FRANCE, Colombes (FR)

(72) Inventors: Eric Jorda, Lyons (FR); Alain Baloche, Annay (FR); Nathalie Gibert, Brignais (FR); Isabelle Birken, Serezin du Rhone (FR); Gilles Barreto, Messimy (FR); Jean-Paul Gamet

(73) Assignee: Arkema France, Colombes (FR)

( * ) Notice: Subject to any disclaimer, the term of this patent is extended or adjusted under 35 U.S.C. 154(b) by 1287 days.

(21) Appl. No.: 16/076,778

(22) PCT Filed: Feb. 13, 2017

(86) PCT No.: PCT/IB2017/000238
§ 371 (c)(1),
(2) Date: Aug. 9, 2018

(87) PCT Pub. No.: WO2017/141117
PCT Pub. Date: Aug. 24, 2017

(65) Prior Publication Data
US 2019/0046994 A1    Feb. 14, 2019

(30) Foreign Application Priority Data
Feb. 16, 2016  (FR) ...................... 1651217

(51) Int. Cl.
*B03D 1/02* (2006.01)
*B03D 1/01* (2006.01)
*C07C 291/00* (2006.01)

(52) U.S. Cl.
CPC ............. *B03D 1/011* (2013.01); *B03D 1/02* (2013.01); *B03D 1/021* (2013.01); *C07C 291/00* (2013.01); *B03D 2201/02* (2013.01); *B03D 2203/02* (2013.01); *B03D 2203/025* (2013.01); *B03D 2203/04* (2013.01); *B03D 2203/06* (2013.01); *B03D 2203/10* (2013.01)

(58) Field of Classification Search
CPC .......... B03D 1/011; B03D 1/016; B03D 1/02; B03D 2201/02; B03D 2203/025; B03D 2203/06; B03D 1/0043; B03D 2203/005; B03D 1/01; B03D 1/16; B03D 1/004; B03D 1/021; B03D 2203/02; B03D 2203/04; B03D 2203/10; C01F 1/00; C09C 3/04; C09C 1/021; C01P 2006/80; B01D 15/00; B01D 21/01; B01D 21/0084; C02F 1/24; C01B 32/60; C07C 291/00

See application file for complete search history.

(56) References Cited

U.S. PATENT DOCUMENTS

| | | | |
|---|---|---|---|
| 4,606,916 A | 8/1986 | Hofinger et al. | |
| 4,995,965 A | 2/1991 | Mehaffey et al. | |
| 6,740,312 B2* | 5/2004 | Chopin | B82Y 30/00 424/490 |
| 8,936,159 B2* | 1/2015 | Gorochovceva | B03D 1/016 209/166 |
| 9,228,089 B2* | 1/2016 | Hellberg | C10L 1/2387 |
| 10,744,517 B2* | 8/2020 | Jorda | B03D 1/016 |
| 11,014,096 B2* | 5/2021 | Sotemann | B03D 1/0043 |
| 2012/0289599 A1* | 11/2012 | Kiesel | C11D 1/72 514/558 |
| 2013/0274492 A1* | 10/2013 | Hellberg | C09K 8/54 554/107 |
| 2015/0096925 A1* | 4/2015 | Hines | B03D 1/01 252/61 |
| 2016/0237379 A1* | 8/2016 | Chow | C11D 11/0023 |
| 2019/0256714 A1* | 8/2019 | Sötemann | B03D 1/011 |
| 2020/0188935 A1* | 6/2020 | Sotemann | B03D 1/0043 |
| 2020/0362100 A1* | 11/2020 | Jorda | C08G 63/6854 |

FOREIGN PATENT DOCUMENTS

| | | |
|---|---|---|
| DE | 19602856 A1 | 7/1997 |
| EP | 0035263 A2 | 9/1981 |
| EP | 0144975 A2 | 6/1985 |
| EP | 1949963 A1 | 7/2008 |
| WO | 2007122148 A1 | 11/2007 |
| WO | 2008089906 A1 | 7/2008 |
| WO | 2011000895 A1 | 1/2011 |
| WO | 2011147855 A2 | 12/2011 |
| WO | 2012089649 A1 | 7/2012 |
| WO | 2015091308 A1 | 6/2015 |

OTHER PUBLICATIONS

International Search Report and Written Opinion for International Application No. PCT/IB2017/000238, dated Jun. 21, 2017—11 pages.

* cited by examiner

*Primary Examiner* — Joseph W Drodge
(74) *Attorney, Agent, or Firm* — RatnerPrestia

(57) ABSTRACT

The present invention relates to the use for ore beneficiation, of at least one derivative of alkoxylated (polyester)amine. The present invention also relates to the flotation pulp and the tailings comprising said product useful for ore beneficiation.

17 Claims, No Drawings

USE OF ALKOXYLATED AMINES AS COLLECTOR AGENTS FOR ORE BENEFICIATION

CROSS-REFERENCE TO RELATED APPLICATIONS

This is the national phase of International Application No. PCT/IB2017/000238, filed 13 Feb. 2017, which claims priority to French Application No. 1651217, filed 16 Feb. 2016. The disclosure of each of these applications is incorporated herein by reference in its entirety for all purposes.

FIELD OF THE INVENTION

The present invention relates to the use of cationic collectors in flotation processes for the beneficiation of ores, more particularly in reverse flotation processes for the beneficiation of ores, specifically for the beneficiation of silicate-containing ores.

BACKGROUND OF THE INVENTION

Flotation consists in extracting minerals out of suspensions of ores, generally aqueous suspensions, by rendering more hydrophobic (less wettable by water) the particles to be floated, using reagents, usually referred to as "collectors". Direct flotation process refers to processes where the floated particles are the ores of value, whereas reverse flotation process refers to processes where the floated particles are the impurities to be extracted out of the ores of value.

Flotation process generally takes place in a cell containing an aqueous suspension of ores to be treated, and a generator of air bubbles. At least one collector is added and the at least one collector adsorbs onto the surface of the particles of minerals or impurities to be removed (case of the reverse flotation), enhancing the attachment of the particles with air bubbles upon collision. The combined air bubbles/particles, less dense than the pulp, go up to the surface, leading to the formation of a froth, which is collected by skimming or via an overflow.

Mineral flotation such as flotation of silica, silicates, feldspath, mica, clays, potash and other minerals, which bear a negative charge at the pH value where the flotation is operated, is typically achieved by using cationic collectors. Cationic collectors are molecules that are at least partly positively charged when added in an aqueous environment at an appropriate pH value.

Hence, the term "cationic collectors" is herein understood to represent organic collector compounds containing at least one amino group. Such cationic collectors are already known, widely used, and include e.g. fatty amines and their salts, fatty propylene polyamines and their salts, alkyl ether amines and alkyl ether diamines and their salts, quaternary ammonium salts, imidazoline derivatives, alkoxylated amines, and the like.

The use of quaternary ammonium compounds as collectors in reverse froth flotation processes for example for calcite ores has long been known. The meaning of the term "reverse froth flotation" is that the froth is used for carrying the gangue mineral rather than carrying the valuable concentrate, i.e. the gangue is recovered in the froth product. See for example U.S. Pat. No. 4,995,965, where calcium carbonate and impurities such as silicate, are separated by floating the silicate and concentrating the calcium carbonate in the remainder, in the presence of collectors such as dialkyl dimethyl quaternary ammonium compounds.

However, dialkyl quaternary products which are currently used for reversed flotation of calcite, for example such as those described in U.S. Pat. No. 4,995,965, have the drawback of being toxic for aqueous organisms and are also regarded as being not readily biodegradable in environment.

DE19602856 proposes to use biodegradable ester quats as collectors in a reverse froth flotation process. These products are quaternary fatty acid alkanolamine ester salts. However, such ester quats were found to degrade, by hydrolysis and/or biologically during the flotation step, releasing fatty acid, particularly in the typical process where the aqueous phase is recycled. In the calcite reverse froth flotation process there is a risk that the fatty acid released may attach to the calcite and float the mineral, resulting in poor yields.

Recently a new class of polymeric ester quats, such as products obtainable by reacting alkanolamines with a mixture of monocarboxylic acids and dicarboxylic acids, has been proposed in international application WO2008/089906.

These products meet the demand of being nontoxic, readily biodegradable products that seem to be sufficiently efficient in flotation. However, they exhibit the same disadvantage as the ester quats mentioned above, with fast release of fatty acid upon hydrolysis, especially when used in a flotation process environment of high pH (around 10) and an elevated temperature (above 30° C.). The release of fatty acid soap can possess a risk as this substance has the opposite collecting properties to the ester quats, thus supporting flotation of the valuable calcite which is then going to waste.

To solve this issue, international application WO2011/147855 proposes another class of oligomeric esterquats. The condensation products described in this patent are represented by the general formula:

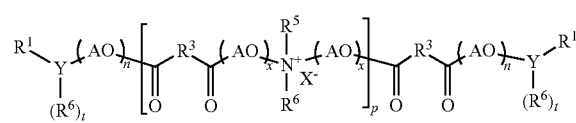

wherein $R^1$ is a hydrocarbyl group having 7-24 carbon atoms, which may be branched or linear, saturated or unsaturated, AO is an alkyleneoxy group having 2-4 carbon atoms, n is a number between 0 and 20, Y is O, C(=O)NH or NZ, where Z is a group $R^2$, where $R^2$ is a $C_1$-$C_4$ alkyl group, preferably $CH_3$, or the benzyl group; provided that when Y is NZ or C(=O)NH, then n is greater than or equal to 1; $R^3$ is an alkylene radical of formula —$(CH_2)_z$—, in which z is an integer from 0 to 10, preferably from 2 to 4, and most preferably 4, and in which the alkylene radical may be substituted by 1 or 2 —OH groups, the group —CH=CH—, a cycloalkylene, a cycloalkenylene or an arylene group; each x independently is a number between 1 and 5, and the sum of all x on average is a number between 2 and 10; $R^5$ is a $C_1$-$C_3$ alkyl group or a group $[AO]_x$; t is 0 when Y is O or C(=O)NH, and t is 1 when Y is NZ; $R^6$ is a hydrocarbyl group, preferably a $C_1$-$C_4$ alkyl group or the benzyl group, and $X^-$ is an anion derived from the alkylating agent $R^6X$; and p is typically a number within the range 1-15, and is on average at least 1, preferably at least 2 and most preferably at least 3; the average value of p depending on the molar ratios of the different compounds used in the reaction mixture, as well as on the reaction conditions.

These products are claimed to avoid release of fatty acid upon hydrolysis. They also present an improved resistance to hydrolysis in a flotation process environment of high pH (around 10) and an elevated temperature (above 30° C.). Anyway, as will be presented in Comparison Example 7 of the present invention, there is still room for improvement concerning the performance of this type of valuable collectors and especially when it comes to resistance to hydrolysis in harsh flotation conditions (high pH and high temperature).

Hence there is a continued need to optimize and/or find alternatives for the reverse froth flotation process of calcium carbonate ores. In this respect it is particularly important that the amount of acid-insoluble material in the product is as low as possible, the yield of product is as high as possible, and that a product of high quality (particularly brightness) is obtained. Due to the huge amount of ore treated per day, it is of particular interest to reach this goal with a dosage of collector as low as possible. It should be realized that reducing the amount of acid-insoluble material and increasing the yield are two mutually conflicting goals.

More specifically, reducing the amount of acid-insoluble material is typically achieved by floating off a large amount of material, but this reduces the yield of the overall beneficiation process, and vice versa.

Apart from calcite ores, there are other valuable ores that contains silicates or other floatable impurities and where highly efficient cationic collectors are of great interest. Phosphate and iron ores beneficiation are other examples of situations where this type of collector can be particularly valuable.

DESCRIPTION OF THE INVENTION

The inventors have now discovered that specific compounds are particularly adapted for ore beneficiation, such compounds being products obtainable by the condensation of an alkoxylated fatty amine of formula (I):

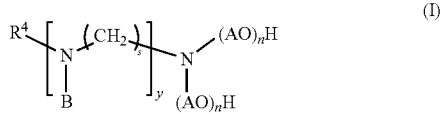

in which:
R$^4$ is chosen from among a hydrocarbyl group having 8-24 carbon atoms, preferably 12 to 24 carbon atoms and a group of formula R$^6$—O-(A'O)$_w$-T-, wherein R$^6$ is a hydrocarbyl group having 8-24 carbon atoms, preferably 12 to 24 carbon atoms, w represents an integer ranging from 0 to 20, preferably from 0 to 10 and more preferably from 0 to 3, A'O is an alkyleneoxy group containing 2-4 carbon atoms; T is alkylene with 1 to 6 carbon atoms, preferably 1 to 4 carbon atoms, most preferably 2 or 3 carbon atoms, AO is an alkyleneoxy group containing 2-4 carbon atoms, preferably 2 carbon atoms, B is chosen from alkyl having 1-4 carbon atoms and benzyl, n represents an integer of between 1 and 20, more preferably between 1 and 10, even more preferably between 1 and 6, limits inclusive, s is 1, 2 or 3, preferably 2 or 3, and y is 0 or 1, or of a product obtainable by partial or total quaternisation of the alkoxylated fatty amine of formula (I), with a dicarboxylic acid or derivative thereof, of formula (II):

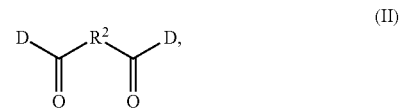

wherein D is chosen from among —OH, —F, —Cl, Br and —OR$^3$, where R$^3$ is a C$_1$-C$_4$ alkyl group; R$^2$ is chosen from the group consisting of:
a direct bond,
a C$_1$-C$_{20}$, linear or branched, saturated or unsaturated hydrocarbon chain optionally substituted by one or more —OH group(s), preferably an alkylene radical of formula —(CH$_2$)$_z$—, in which z is an integer from 1 to 20, preferably from 1 to 10, preferably from 2 to 6, and most preferably 4, a substituted alkylene radical wherein said alkylene radical is substituted by 1 or 2 —OH groups, an alkenylene radical having from 1 to 20, preferably from 1 to 10 carbon atoms, a substituted alkenylene radical, wherein said alkenylene radical is substituted by 1 or 2 methyl and/or methylene groups,
a cycloalkylene,
a cycloalkenylene and
an arylene group.

It is to be understood that the dicarboxylic acids or derivatives thereof of formula (II) also include their corresponding anhydride forms.

It is also to be understood that when compound of formula (I) contains more than one (AO)$_n$ group, the value of the integers n may be the same or different, independently from one another. Similarly, when more than one y is present, all "y" are, independently form one another, identical or different.

Optionally said product which is obtainable by reaction between the dicarboxylic acid or derivative thereof of formula (II) and the alkoxylated fatty amine of formula (I), has undergone a further reaction step wherein part, or all, of the nitrogen atoms are quaternised by reaction with an alkylating agent R$^5$X, where R$^5$ is a hydrocarbyl group, preferably a C$_1$-C$_4$ alkyl group or the benzyl group, and X is any leaving group known in the art using alkylating agents, and preferably X is generally chosen from among halogens, sulphates, carbonates, and the like.

Formula (1) here-under is a possible representation of such reaction products obtainable by the condensation of an alkoxylated fatty amine of the formula (I), or its partially or totally quaternised corresponding compound, with a dicarboxylic acid or a derivative thereof of formula (II) as defined above, optionally followed by a further reaction step wherein part or all of the nitrogen atoms are quaternised by reaction with an alkylating agent R$^5$X, where R$^5$ and X are as defined above.

Therefore, and as a first aspect, the present invention relates to the use for ore beneficiation, of at least one compound of general formula (1):

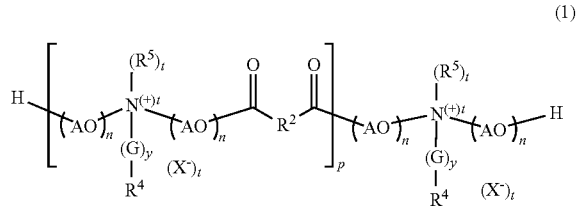

wherein:
p ranges from 1 to 15, preferably from 1 to 10, more preferably from 1 to 5,
G represents a group of formula (III)

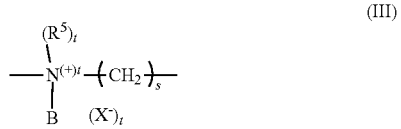

in which
B, $R^5$, X, s are as defined above, t is 0 or 1, wherein the group —$(CH_2)_s$— is a spacer between the two nitrogen atoms to which it is linked, and
$R^2$, $R^4$, $R^5$, X, AO, n, t, y are as defined above.

As said above the reaction product which is obtainable by reaction between the dicarboxylic acid or derivative thereof of formula (II) and the alkoxylated fatty amine of formula (I), with optional quaternisation, is useful for ore beneficiation, and more especially is useful as a collector for flotation, more specifically for flotation of silicates, and even more specifically for beneficiation of ores containing silicate impurities and preferably for the beneficiation of calcite ores.

In one particular embodiment, the alkoxylated fatty amine is of formula (IA):

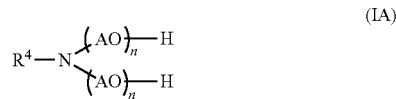

which is compound of formula (I) wherein y represents 0, and $R^4$, AO and n are as defined above, as well as its partially or totally quaternised corresponding compound.

In this embodiment, the invention relates to the use for ore beneficiation, of a product obtainable by the condensation of an alkoxylated fatty amine of the formula (IA), or its partially or totally quaternised corresponding compound, with a dicarboxylic acid or a derivative thereof of formula (II) as defined above, optionally followed by a further reaction step wherein part or all of the nitrogen atoms are quaternised by reaction with an alkylating agent $R^5X$, where $R^5$ and X are as defined above, and therefore when more than one t is present, all "t" are, independently form one another, identical or different.

For this embodiment where the condensation product described above is obtained from the alkoxylated fatty amine of formula (IA), the said product may be represented by the general formula (1A):

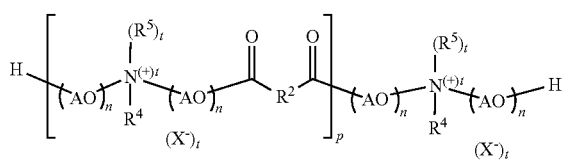

wherein AO, n, p, t, $R^2$, $R^4$, $R^5$ and X are as defined above, formula (1A) being formula (1) wherein y=0.

It is to be understood that there might be molecules present in the product mixture that are not completely reacted, but the products of formula (1A) are the preferred compounds of interest for the use of the present invention. Similarly when using alkoxylated amines of general formula (I), there might be molecules present in the product mixture that are not completely reacted, but the oligomers (condensation products) are the products of interest regarding the use of the present invention.

This type of products has been already described in the prior art, for example in EP0144975, EP0035263 and WO11000895, however for hair care application or as textile softeners or corrosion inhibitors, that is to say applications that are totally different from the use encompassed by the present invention.

The above described dicarboxylic acid derivative of general formula (II) may be any dicarboxylic acid or dicarboxylic acid derivative or anhydride known by the skilled in the art, and typically a dicarboxylic acid, a dicarboxylic acid halide, e.g. chloride, a diester of a dicarboxylic acid, or a cyclic anhydride of a dicarboxylic acid. Most suitable derivatives are the dicarboxylic acids and their corresponding cyclic anhydrides.

Illustrative examples of dicarboxylic acid derivatives of general formula (II) include oxalic acid, malonic acid, succinic acid, glutaric acid, glutaconic acid, adipic acid, muconic acid, pimelic acid, phthalic acid, terephthalic acid, tetrahydrophthalic acid, malic acid, maleic acid, fumaric acid, suberic acid, mesaconic acid, sebacic acid, azelaic acid, tartaric acid, itaconic acid, glutinic acid, citraconic acid, brassylic acid, dodecanedioic acid, traumatic acid, thapsic acid, their corresponding acid chlorides, their corresponding methyl or ethyl esters, and their corresponding cyclic anhydrides, as well as mixtures thereof.

Preferred dicarboxylic acid derivatives of general formula (II) are chosen from among oxalic acid, malonic acid, succinic acid, glutaric acid, adipic acid, pimelic acid, phthalic acid, terephthalic acid, tetrahydrophthalic acid, malic acid, tartaric acid, itaconic acid, their corresponding acid chlorides, their corresponding methyl or ethyl esters, and their corresponding cyclic anhydrides, as well as mixtures thereof.

Alkoxylated fatty amines of formula (I) are either available or may be prepared according to known process from the literature, and for example may be for example easily prepared by alkoxylation of fatty amines.

Illustrative examples of suitable fatty amines for use as starting materials for the preparation of alkoxylated fatty amines of formula (I) include, but are not limited to, (fatty alkyl) monoamines or (fatty alkyl) etheramines according to formula $R^4NH_2$, and (fatty alkyl)methyl diamines having the following general formula:

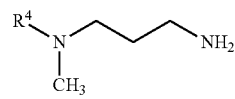

wherein $R^4$ is as defined above.

More specific examples of the above-mentioned amines include, but are not limited to, 2-ethylhexyl amine, 2-propylheptyl amine, n-octyl amine, n-decyl amine, n-dodecyl amine, (coco alkyl) amine, (palm oil alkyl) amine, n-tetradecyl amine, n-hexadecyl amine, n-octadecyl amine, oleyl amine, (tallow alkyl) amine, (hydrogenated tallow alkyl) amine, (rape seed alkyl) amine, (soya alkyl) amine, erucyl amine, N-(n-decyl)-N-methyl-trimethylene diamine, N-(n-dodecyl)-N-methyl-trimethylene diamine, N-(coco alkyl)-N-methyl-trimethylene diamine, N-(rape seed alkyl)-N-methyl-trimethylene diamine, N-(soya alkyl)-N-methyl-trimethylene diamine, N-(tallow alkyl)-N-methyl-trimethylene diamine, N-(hydrogenated tallow alkyl)-N-methyl-trimethylene diamine, N-erucyl-N-methyl trimethylene diamine, and iso-tridecyloxypropylamine, as well as mixtures thereof.

According to an embodiment of the invention, the above-mentioned amines are fatty amines obtained from natural (vegetable or animal) oils or acids and mixtures thereof, e.g. coco fatty acid, tallow fatty acid, rape seed oils, soya oils, palm oils.

These fatty amines are then typically alkoxylated with 2 to 20, preferably 2 to 10 EO (ethyleneoxy units), and/or 2 to 20, preferably 2 to 10 PO (propyleneoxy units), and/or 2 to 20, preferably 2 to 10 BO (butyleneoxy units). Blocks with EO are generally added first and PO and/or BO last, or blocks with PO and/or BO added first and EO last, or with mixtures of EO and PO and/or BO to produce randomly alkoxylated products of the general formula (I). The alkoxylation may be performed by any suitable method known in the art by using e.g. an alkaline catalyst, such as potassium hydroxide (KOH), or an acid catalyst.

Examples of commercial products of formula (I) include Noramox® SD20, Noramox® SD15, Noramox® S11, Noramox® S5, Noramox® S7, Noramox® S2, Noramox® SH2, Noramox® O2, Noramox® O5, Noramox® C2, Noramox® C5, Noramox® C15. All such commercial products are available from CECA S.A. Other examples of commercial products of formula (I) include Tomamine® E-17-5 and Tomamine® E-T-2 available from Air Products.

A suitable method for the preparation of the products for use in the present invention comprises the steps of mixing at least one compound of formula (II) as defined above and at least one compound of formula (I) as defined above, and running an esterification condensation reaction between the compounds in the mixture. When a quaternary product is desired, the preparation process further comprises at least one step consisting in adding an alkylating agent to the condensation reaction product and running the said quaternisation reaction of the condensation product.

The esterification condensation reaction taking place between the compounds of formula (II) and of formula (I) is a reaction well-known per se in the art. The reaction is preferably being performed in the presence of an esterification catalyst, such as a Brønstedt acid or Lewis acid, for example methanesulphonic acid, para-toluenesulphonic acid, hypophosphoric acid, citric acid or boron trifluoride ($BF_3$).

When a dicarboxylic acid derivative of formula (II) wherein D is O—$R^3$ is used, the reaction is a transesterification, which alternatively could be performed in the presence of an alkaline catalyst. Alternatively, other conventional techniques known by the person skilled in the art could be used starting from other derivatives of the dicarboxylic acids, such as from their anhydrides or their acid chlorides.

As would also be clear to a person skilled in the art, the different esterification reactions may take place with or without solvents added. If solvents are present during the reaction, the solvents should be inert to esterification, e.g. toluene or xylene, and the like.

The esterification condensation reaction between the components (II) and (I) is suitably realized with heating of the mixture at a temperature typically ranging from 120° C. to 280° C. for a period of time ranging from 2 to 20 hours, optionally at a reduced pressure, e.g. of from 500 Pa to 20000 Pa.

When t is 0 in formula (1), the product is a tertiary polyesteramine compound, and when t is 1 the product is a polyester polyquaternary ammonium compound, resulting from quaternisation of the compound where t is 0. Quaternisation is a reaction type that is well-known in the art. For the quaternisation step, an alkylating agent, e.g. of formula $R^5X$, is generally selected from the group consisting of methyl chloride, methyl bromide, methyl iodide, dimethyl sulphate, diethyl sulphate, dimethyl carbonate and benzyl chloride, the most preferred alkylating agents being methyl chloride, dimethyl sulphate, dimethyl carbonate or benzyl chloride, and mixtures thereof, preferably methyl chloride and/or dimethylsulphate.

As stated above, the quaternisation could suitably be performed on the condensation product between the alkoxylated fatty amine and the dicarboxylic acid derivative. As an alternative synthesis route, the quaternisation of the alkoxylated fatty amine (I) could be performed as a first step, which would then be followed by an esterification reaction with (II).

Quaternisation reactions are normally performed in water and/or in an organic solvent, such as isopropanol (IPA) or ethanol, or in mixtures thereof. Other alternative solvents could be ethylene glycol monobutyl ether, di(ethylene glycol) monobutyl ether (BDG), and other ethylene- and propylene glycols, such as monoethylene glycol (MEG) and diethylene glycol (DEG). The reaction temperature of the quaternising reaction is suitably in the range of from 20° C. to 100° C., preferably at least 40° C., more preferably at least 50° C. and most preferably at least 55° C., and preferably at most 90° C.

The expression "totally quaternised" in the present description is equivalent to "all of the nitrogen atoms are quaternised" and means that the total amount of basic nitrogen per gram of compound is less than or equal to 0.2 mmol, preferably less than or equal to 0.1 mmol, more preferably less than or equal to 0.05 mmol.

As a consequence, the heating is preferably stopped when the amount of basic nitrogen is less or equal to 0.2 $mmol.g^{-1}$, preferably less than or equal to 0.1 $mmol.g^{-1}$, more preferably less than or equal to 0.05 $mmol.g^{-1}$, for example as measured by titration with 0.2 N hydrochloric acid in isopropanol or any other suitable method known by se in the art.

In an embodiment, preferred compounds of formula (1A) are those wherein:

$R^2$ is chosen from the group consisting of an alkylene radical of formula —$(CH_2)_z$—, in which z is an integer from 1 to 20, preferably from 1 to 10, preferably from 2 to 6, and most preferably 4, $R^4$ is chosen from among a hydrocarbyl group having 8 to 24 carbon atoms, preferably 12 to 24 carbon atoms, and AO, n, p, t, $R^5$ and X being as defined above.

According to another embodiment, preferred compounds of formula (1) are those wherein all "t" are equal to 1, that is to say, all nitrogen atoms are quaternised, all other variable groups and integers being as defined above.

According to another embodiment, preferred compounds of formula (1) are those wherein all "t" are equal to 1, and $R^5$ is chosen from among methyl and ethyl, all other variable groups and integers being as defined above.

According to still another embodiment, preferred compounds of formula (1) are those wherein all "t" are equal to 1, $R^5$ is chosen from among methyl and ethyl, and X is chosen from among halogens and sulphates (e.g. methosulphates), all other variable groups and integers being as defined above.

According to a further embodiment, preferred compounds of formula (1) are those wherein all "n", independently from one another, are identical or different chosen from 1 to 6, inclusive limits, p ranges from 1 to 10, inclusive limits, and all other variable groups and integers being as defined above.

Products for use as collectors for ore beneficiation according to the invention, wherein all nitrogen atoms of the said product are quaternary nitrogen atoms, are preferred.

In a specific embodiment of the present invention, the molar ratio between reactants (I) and (II) is 2:1 to 1:2, preferably 1.5:1 to 1:1.5, and most preferably 1.4:1 to 1:1.4 in order to produce suitable flotation collectors. According to another specific embodiment of the present invention, the molar ratio between reactants (I) and (II) is 2:1 to 1:1, preferably 2:1 to 1.2:1, and most preferably 2:1 to 1.3:1 in order to produce suitable flotation collectors.

It has surprisingly been discovered that the products for use as collectors for ore beneficiation according to the invention do present an improved efficiency as compared to the known prior art collectors. Improved efficiency (or better efficiency) is for example illustrated by higher flotation yields at same dosage or same flotation yields at lower dosage.

Among the most preferred products for use as collectors for ore beneficiation according to the invention may be cited the polymer of adipic acid with ethoxylated coco alkyl amine (5OE), chloromethane quaternised, the polymer of adipic acid with ethoxylated tallow alkyl amine (11OE), chloromethane quaternised, the polymer of adipic acid with ethoxylated tallow alkyl amine (5OE), chloromethane quaternised.

Polymers of adipic acid with ethoxylated $C_{16}$-$C_{18}$ and $C_{18}$ unsaturated amine (or tallow alkyl amine or palm oil alkyl amine), chloromethane quaternised, are new and therefore form part of the present invention, as well as polymers of adipic acid with ethoxylated $C_8$-$C_{16}$ and $C_{18}$ unsaturated amine (or coco alkyl amine), chloromethane quaternised, polymers of adipic acid with ethoxylated $C_{18}$ unsaturated amine (oleyl amine), chloromethane quaternised, polymers of maleic anhydride with ethoxylated $C_{16}$-$C_{18}$ and $C_{18}$ unsaturated amine (or tallow alkyl amine or palm oil alkyl amine), chloromethane quaternised, polymers of maleic anhydride with ethoxylated $C_8$-$C_{16}$ and $C_{18}$ unsaturated amine (or coco alkyl amine), chloromethane quaternised, polymers of maleic anhydride with ethoxylated $C_{18}$ unsaturated amine (oleyl amine), chloromethane quaternised, polymers of sebacic acid with ethoxylated $C_{16}$-$C_{18}$ and $C_{18}$ unsaturated amine (or tallow alkyl amine or palm oil alkyl amine), chloromethane quaternised, polymers of sebacic acid with ethoxylated $C_8$-$C_{16}$ and $C_{18}$ unsaturated amine (or coco alkyl amine), chloromethane quaternised, polymers of sebacic acid with ethoxylated $C_{18}$ unsaturated amine (oleyl amine), chloromethane quaternised, polymers of glutaric acid with ethoxylated $C_{16}$-$C_{18}$ and $C_{18}$ unsaturated amine (or tallow alkyl amine or palm oil alkyl amine), chloromethane quaternised, polymers of glutaric acid with ethoxylated $C_8$-$C_{16}$ and $C_{18}$ unsaturated amine (or coco alkyl amine), chloromethane quaternised, polymers of glutaric acid with ethoxylated $C_{18}$ unsaturated amine (oleyl amine), chloromethane quaternised, and also the corresponding polymers, dimethyl or diethyl sulphate quaternised.

Other advantages linked to the use of the products for use as collectors for ore beneficiation according to the invention are visible through the better preservation of efficiency in harsh flotation conditions (such as pH value of 10 or higher), and elevated pulp temperatures (such as temperatures of 30° C. or higher). An example of standard conditions for flotation can be found in example 5 of international application WO2011/147855 where natural pH of the pulp is 8.5 and temperature is around 20° C. for the beneficiation of calcite by reverse flotation. As there is generally no equipment for pH and temperature control at the industrial scale, it is particularly useful to have robust collectors that can handle pH change of the pulp (depending on ore characteristics) and temperature rise during hot summers, without loss of efficiency.

Therefore, the present invention deals with the use of at least one collector which is a product obtainable by the condensation of an alkoxylated fatty amine of formula (I) or its partially or totally quaternised corresponding compound, and a dicarboxylic acid derivative of formula (II) as defined above, said condensation being optionally followed by a further reaction step wherein part or all of the nitrogen atoms are quaternised by reaction with an alkylating agent $R^5X$, where $R^5$ and X are as defined above, for the beneficiation by direct or reverse, preferably reverse, flotation of an aqueous suspension of ores containing minerals.

The collector for use in the present invention is efficient either in direct flotation processes or in reverse flotation processes. The collector as defined above for use in the present invention is particularly adapted for the beneficiation of aqueous suspensions of ores using a reverse flotation process.

The collector for use in the present invention may be used in concomitantly, after or before one or more other collectors as defined above and/or conventional collector agents known in the art.

Examples of conventional collector agents that may be used in the present invention include, but are not limited to, fatty amines and their salts, as well as their alkoxylated derivatives, fatty poly(alkylene amines) and their salts, e.g. poly(ethylene amines), poly(propylene amines) and their salts, as well as their alkoxylated derivatives, fatty amidopolyamines, and their salts, as well as their alkoxylated derivatives, fatty amidopoly(alkyleneamines), and their salts, as well as their alkoxylated derivatives, fatty imidazolines and their salts, as well as their alkoxylated derivatives, N-fatty alkyl amino carboxylic acid and their salts, e.g. N-fatty alkyl amino propionic acid and their salts, alkyl ether amines and alkyl ether diamines and their salts, quaternary ammonium compounds, e.g. fatty quaternary ammonium compounds, mono(fatty alkyl) quaternary ammonium compounds, di(fatty alkyl) quaternary ammonium compounds, such as those described in WO 2007/122148 A1, and the like.

A "polyamine" in the meaning of the present invention is a compound comprising two or more amine groups, the amine groups possibly being substituted, i.e. the two or more amine groups may be identical or different and be primary, secondary or tertiary amine groups.

Specific examples of conventional cationic collector agents that may be used in the present invention include, without any limitation, dicoco-dimethyl ammonium chloride (CAS RN 61789-77-3), coco-dimethylbenzyl ammonium chloride (CAS RN 61789-71-7), tallow dimethyl benzyl ammonium chloride (CAS RN 61789-75-1), ethoxylated tallow monoamine, 1,3-propanediamine-N-tallow diacetate (CAS RN 68911-78-4), N,N',N'-tri-hydroxy-ethyl N-tallow propylene diamine (CAS RN 61790-85-0), N,N',N'-tri-hydroxyethyl N-oleyl propylene diamine (CAS RN 103625-43-0), N,N',N'-tri-hydroxyethyl N-lauryl propylene diamine (CAS RN 25725-44-4), fatty alkyl imidazoline obtained by condensation of diethylenetriamine and oleic fatty acid (CAS RN 162774-14-3), N,N',N'-tri-hydroxyethyl N behenyl-propylene diamine (CAS RN 91001-82-0), isodecyloxypropyl-1,3-diaminopropane (CAS RN 72162-46-0), N,N-di (tallow carboxyethyl)-N-hydroxyethyl-N-methyl ammonium methylsulphate (CAS RN 91995-81-2), N-coco-β-aminopropionic acid (CAS RN 84812-94-2), N-lauryl-β-aminopropionic acid (CAS RN 1462-54-0), N-myristyl-β-aminopropionic acid (CAS RN 14960-08-8), their addition salts with acid(s), sodium salt of N-lauryl-β-aminopropionic acid (CAS RN 3546-96-1), triethanolamine salt of N-lauryl-β-aminopropionic acid (CAS RN 14171-00-7), triethanolamine salt of N-myristyl-β-aminopropionic acid (CAS RN 61791-98-8), as well as mixtures of two or more of the above compounds, in all proportions, and the like.

Etheramines" and "etherdiamines" in the meaning of the present invention are compounds comprising at least one ether group and respectively a $NH_2$ terminal group and a $NH_2$ terminal group as well as another primary, secondary or tertiary amine group.

Other examples of conventional collectors include anionic collector agents, an among them, as non-limiting examples thereof, fatty carboxylic acids and derivatives thereof, sulphonated fatty acids and derivatives thereof, phosphoric acid esters and derivatives thereof, typically alkoxylated derivatives thereof, such as compounds known under the trade name Melioran® sold by the CECA S.A. Company, and more specifically Melioran® P312.

The collector for use in the present invention, for beneficiation by flotation of aqueous suspensions of ores, may consist in one or more compounds as defined above, alone or in combination with one or more known collectors as herein-before described. Moreover, such compounds may further be formulated with any conventional additive(s) known in the art of flotation.

Non limitative examples of such additives are pH-adjusting agents, such as sodium or potassium carbonate and sodium or potassium hydroxide, phosphoric acids, sulfuric acid and fluosilicic acid; solvents (water, organic solvent(s) and mixtures thereof); depressants, such as starch, quebracho, tannin, dextrin and guar gum, and polyelectrolytes, such as polyphosphates and water glass, which have a dispersant effect, often combined with a depressant effect. Other conventional additives may be chosen from among hydrocarbons (various hydrocarbon cuts), frothers (foaming agents), such as methyl isobutyl carbinol, triethoxy butane, pine oil, terpineol and polypropylene oxide and its alkyl ethers, among which methyl isobutyl carbinol, triethoxy butane, pine oil, terpineol, are preferred frothers. By way of non-limiting examples, preferred conventional additives are generally frothers, among which terpineol is the most commonly used.

The use of the present invention is particularly efficient for the beneficiation of all types of impurities containing-ores, and more precisely for the beneficiation of carbonates (calcium and/or magnesium carbonates), phosphates and iron ores, the beneficiation of calcium carbonates being particularly preferred.

The use of the present invention is particularly appropriate for the beneficiation of all types of calcium carbonates (natural or ground), such as limestone, chalk, marble, calcite, calcium carbonate-containing materials (70% minimum content of $CaCO_3$), alkaline earth metal containing calcium carbonates (e.g. sodium calcium carbonate or gaylussite), magnesium carbonates (e.g. magnesium carbonate containing calcium carbonates, such as dolomite), beryllium carbonates, strontium carbonates, barium carbonates, radium carbonates, as well as mixtures thereof.

"Natural calcium carbonate" in the meaning of the present specification is a calcium carbonate (calcite) obtained from natural sources, such as marble, limestone, or chalk. "Ground calcium carbonate" (GCC) in the meaning of the present invention is a natural calcium carbonate that is processed through a wet and/or dry treatment such as grinding, screening and/or fractionating, for example by a cyclone or classifier.

Other ores that can be efficiently beneficiated using the collectors according to the present invention include wollastonite, barite, titanium oxides (e.g. rutile, anatase, brookite), kaolin, kaolinitic clays (soft white clays composed mainly of kaolinite), calcined kaolinitic clays, montmorillonite, sepiolite, talc, diatomaceous earths, aluminium oxides (e.g. $\alpha$-$Al_2O_3$, $\gamma$-$Al_2O_3$), aluminium oxides containing other elements, such as sodium (e.g. diaoyudaoite), as well as other oxides, sulphates and sulphides, such as zinc oxides, zirconium dioxides, tin dioxide, lead carbonate, barium sulphate, and zinc sulphide, including mixtures of two or more of the foregoing in all proportions.

The above mentioned ores are often defined as "white pigments". In the meaning of the present invention, a white pigment is a pigment that has a white colour. The white colour of the white pigments is predominately based on the relatively low light absorption in combination with an unselective light scattering of the visual light at the pigments. The white pigments in the present invention are inorganic white pigments that may be naturally or synthetically obtained.

The collectors for use in the present invention are also efficient for the direct or reverse froth flotation of "non-white pigments" (as opposed to the above-listed white pigments). Non-white pigments include, however not being limited to, ores chosen from among phosphates, potassium chloride, metal-containing ores, wherein "metal" stands for e.g. iron, platinum, aluminium, nickel, copper, and the like.

The minerals that are efficiently eliminated, or at least the content of which in the ores is significantly reduced by flotation, may be of any type known by the skilled in the art, and preferably provided they are negatively charged at the pH where the flotation is operated. Generally speaking said minerals include, but are not limited to, insoluble graphite, iron sulphides (e.g. pyrite, marcasite, magnetopyrite, pyrrhotite, mackinawite), iron oxides (e.g. wüstite, magnetite), iron hydroxides and iron oxyhydroxides (e.g. bernalite, goethite, lepidocrocite, feroxyhyte, ferrihydrite, schwertmannite, akaganeite), silica, silicates (neosilicates, sorosilicates, cyclosilicates, inosilicates, phyllosilicates, tectosilicates and/or amorphous silicates, such as zircon, willemite, olivine, mullite, forsterite, aluminosilicates, fayalite, ilavite, gehlenite, epidote, kornerupine, benitonite, beryl, tourmaline, enstatite, wollastonite, rhodenite, diopside, amphibolite, grunerite, cummingtonite, actinolithe, hornblende, talc, kaoline, kaolinitic clay, calcined kaolinitic clay, halloysite, dickite, vermiculite, nontronite, sepiolite or montmorillonite, mica minerals, biotite, muscovite, phlogopite, lepidolite or glauconite, clinochlore, quartz, tridymite, cristobalite, feldspar minerals, diatomaceous earth or opale), mica, clays, potash (potassium chloride), and the like, as well as mixtures thereof. Preferably the minerals that are efficiently eliminated, or at least the content of which in the ores is significantly reduced, by direct or reverse, preferably reverse, froth flotation of ores, include silicates, preferably quartz minerals, such as quartz, tridymite and/or cristobalite, more preferably quartz, as well as mixtures of quartz and one or more additional silicates, even more preferably quartz alone.

The use of the present invention is particularly well adapted for the beneficiation of calcium carbonate, and typically where the minerals (impurities) that are efficiently eliminated comprise silicates, preferably quartz.

The total content of the at least one product obtainable by the condensation of an alkoxylated fatty amine of formula (I) or its partially or totally quaternised corresponding compound, and a dicarboxylic acid derivative of formula (II) as defined above, said condensation being optionally followed by a further reaction step wherein part or all of the nitrogen atoms are quaternised by reaction with an alkylating agent $R^5X$, where $R^5$ and X are as defined above, for use in the beneficiation process by flotation of an aqueous suspension of ores according to the present invention, may vary within wide limits depending on the nature of the ores to be purified and the nature and amount of the impurities contained therein.

Generally the total amount of such a product added to the flotation process ranges of from 1 ppm to 5000 ppm, preferably 10 ppm to 5000 ppm, preferably from 20 ppm to 2 000 ppm, more preferably from 30 ppm to 1 000 ppm, and most preferably from 50 ppm to 800 ppm by weight relative to the amount of ore(s) to be beneficiated.

According to another aspect, the invention relates to a flotation pulp comprising water, ground ore containing silicate impurities and at least one product obtainable by the condensation of an alkoxylated fatty amine of formula (I) or its partially or totally quaternised corresponding compound, and a dicarboxylic acid derivative of formula (II) as defined above, said condensation being optionally followed by a further reaction step wherein part or all of the nitrogen atoms are quaternised by reaction with an alkylating agent $R^5X$, where $R^5$ and X are as defined above.

According to a preferred embodiment the flotation pulp of the invention comprises at least one or both, preferably both, of the following characteristics:
  a solid weight content of the pulp between 5 wt % and 80 wt %, preferably between 10 wt % and 70 wt % and more preferably between 20 wt % and 60 wt %, most preferably between 25 wt % and 55 wt %,
  a collector content between 0.001 wt % and 0.5 wt %, preferably between 0.002 wt % and 0.2 wt % and more preferably between 0.003 wt % and 0.1 wt %, and most preferably between 0.005 and 0.08 wt % based on the solids weight content of the pulp.

According to still another aspect, the present invention relates to the tailings resulting from the process of ore beneficiation. More particularly; the present invention relates to tailings comprising floated impurities, preferably silicates, and at least one collector product obtainable by the condensation of an alkoxylated fatty amine of formula (I) or its partially or totally quaternised corresponding compound, and a dicarboxylic acid derivative of formula (II) as defined above, said condensation being optionally followed by a further reaction step wherein part or all of the nitrogen atoms are quaternised by reaction with an alkylating agent $R^5X$, where $R^5$ and X are as defined above.

According to a preferred aspect the present invention relates to tailings comprising from 50 wt % to 99.995 wt %, and preferably from 80 wt % to 99.9 wt % of floated impurities, and from 0.005 wt % to 35 wt %, preferably from 0.05 wt % to 5 wt %, of at least one collector as defined above, relative to the total weight of the dried tailings. Dried tailings are obtained after drying in an oven at 90° C., during 16 hours, at atmospheric pressure.

EXAMPLES

The invention will be better understood thanks to the following examples that are provided for illustrative purpose only without any intention to limit the scope of the sought protection defined by the annexed claims. In the whole description, examples and claims, all value ranges are to be understood "limits inclusive" (i.e. limits are included within said ranges), unless specifically otherwise depicted.

Acid Value Measurement Method:

In all the following examples, acid value is measured by potentiometric titration using potassium hydroxide solution as the reagent and isopropyl alcohol as a solvent. In a 250 mL beaker, about 10 g of sample to analyse is precisely weighed (Sw, precision to the mg) and 70 mL of isopropyl alcohol are added. The mixture is agitated and heated gently if necessary to get a homogeneous sample. The titrator combined glass reference electrode is introduced into the solution, which is then agitated with a magnetic stirrer. The acid-base titration of the sample is performed using 0.1 N aqueous potassium hydroxide (KOH) solution and the pH evolution is recorded on the titrator. The equivalent point is graphically determined using methods known to the skilled in the art, and the volume ($V_{KOH}$, in mL) of potassium hydroxide solution used to reach this point determined. The acid value (AV) is then obtained according to the following calculation:

$$AV = \frac{[\text{Normality of } KOH \text{ solution (mol/L)}] \times 56.1 \times V_{KOH}}{Sw}$$

Example 1: Synthesis of a Collector A (According to the Invention)

In a 4 L round bottom flask are introduced 2025.8 g of ethoxylated coco alkyl amine (5OE) supplied by CECA S.A. under the trade name Noramox® C5 with 0.2 g of a 50 wt % aqueous solution of hypophosphorous acid. The mixture is heated to 80° C. with nitrogen bubbling. The bubbling is stopped and 503.7 g of adipic acid are then introduced under agitation.

After 15 minutes, the mixture temperature is raised up to 160° C. in a 1 hour time and the pressure in the vessel is progressively lowered until a pressure of 6.67 kPa (50 mm Hg) is reached. The temperature and low pressure are maintained during 1 hour and then the temperature is raised up to 200° C. for 4 hours. Then the temperature is again raised to 220° C. and maintained until almost all of the acid is consumed (Acid Value <5).

The system is then cooled down to recover the sought esteramine product. In a second step, in a 6 L glass reactor, are introduced 2000 g of the esteramine product obtained in the previous step with 300 g of isopropyl alcohol. Methyl chloride is added until the pressure in the vessel reaches 290 kPa. The temperature is maintained at 80° C.-85° C. until complete reaction has occurred.

Complete reaction is achieved when the total amount of basic nitrogen is less or equal to 0.2 mmol.g$^{-1}$, as measured by titration with 0.2 N hydrochloric acid in isopropanol. The reactor is then let to cool down to 65° C. and the pressure back to atmospheric. Nitrogen is bubbled during 2 hours in the mixture before recovering the product, which corresponds to the polymer of adipic acid with ethoxylated coco alkyl amine (5OE), chloromethane quaternised.

Example 2: Synthesis of a Collector B (According to the Invention)

In a 4 L round bottom flask are introduced 1872 g of ethoxylated tallow alkyl amine (11OE) supplied by CECA S.A. under the trade name Noramox® S11 with 0.3 g of a 50 wt % aqueous solution of hypophosphorous acid. The mixture is heated until 80° C. with nitrogen bubbling. Bubbling is stopped and 184 g of adipic acid are introduced.

After 15 minutes, the mixture temperature is raised up to 160° C. in a 1 hour time and the pressure in the vessel is progressively until a pressure of 6.67 kPa (50 mm Hg) is reached. The temperature and low pressure are maintained during 1 hour and then the temperature is raised up to 200° C. for 4 hours. Then the temperature is again raised to 220° C. and maintained until almost all of the acid is consumed (Acid Value <5).

The system is then cooled down to recover the sought esteramine product. In a second step, in a 6 L glass reactor, are introduced 2000 g of the esteramine product obtained in the previous step with 300 g of isopropyl alcohol. Methyl chloride is added until the pressure in the vessel reaches 290 kPa. The temperature is maintained at 80° C.-85° C. until complete reaction has occurred.

Complete reaction is achieved when the total amount of basic nitrogen is less or equal to 0.2 mmol.g$^{-1}$, as measured by titration with 0.2 N hydrochloric acid in isopropanol. The reactor is then let to cool down to 65° C. and the pressure back to atmospheric. Nitrogen is bubbled during 2 hours in the mixture before recovering the product, which corresponds to the polymer of adipic acid with ethoxylated tallow alkyl amine (11OE), chloromethane quaternised.

Example 3: Synthesis of a Collector C (According to the Invention)

In a 4 L round bottom flask, are introduce 2201.7 g of ethoxylated tallow alkyl amine (5OE) supplied by CECA S.A. under the trade name Noramox® S5 and 0.2 g of a 50 wt % aqueous solution of hypophosphorous acid.

The mixture is heated to 80° C. with nitrogen bubbling. The bubbling is stopped and 503.7 g of adipic acid are then introduced under agitation.

After 15 minutes, the mixture temperature is raised up to 120° C. in a 1 hour time and the pressure in the vessel is progressively lowered until a pressure of 6.66 kPa (50 mm Hg) is reached. The temperature is raised up to 160° C. and temperature and pressure are maintained until almost all of the acid is consumed (Acid Value <5).

The system is then cooled down to recover the sought esteramine product.

In a second step, in a 6 L glass reactor, are introduced 2038.9 g of the esteramine product obtained in the previous step with 305.8 g of isopropyl alcohol. Methyl chloride is added until the pressure in the vessel reaches 290 kPa. The temperature is maintained at 80° C.-85° C. until complete reaction has occurred.

Complete reaction is achieved when the total amount of basic nitrogen is less or equal to 0.2 mmol.g$^{-1}$, as measured by titration with 0.2 N hydrochloric acid in isopropanol. The reactor is then let to cool down to 65° C. and the pressure back to atmospheric. Nitrogen is bubbled during 2 hours in the mixture before recovering the product, which corresponds to the polymer of adipic acid with ethoxylated tallow alkyl amine (5OE), chloromethane quaternised.

Example 4: Synthesis of Esterquat FC According to Example 2 of WO 2011/147855 (Comparative Example)

Alfol® C16 (378.4 g), adipic acid (461.2 g) and methyldiethanolamine (285.8 g) are added to a round bottom flask, fitted with a condenser, a thermometer, a heating mantel, a nitrogen inlet and a mechanical stirrer. The temperature of the reaction mixture is gradually raised to 160° C. and the water produced during the reaction is distilled off. The distillation of the water starts at 154° C. and is continued for 1.5 hour at 164° C.-175° C., under atmospheric pressure. Then vacuum is applied (6.67 kPa (50 mm Hg) pressure in the vessel) and distillation is continued for 5 more hours. The progress of the reaction is evaluated by the determination of the acid value.

For the quaternisation reaction, 2125 g of esteramine product obtained in the previous step and 534 g of isopropyl alcohol are introduced in a 6 L glass reactor. Methyl Chloride is then introduced until the pressure in the vessel reaches 290 kPa. Temperature is maintained at 80-85° C. until complete reaction has occurred.

Complete reaction is achieved when the total amount of basic nitrogen is less or equal to 0.2 mmol.g$^{-1}$, as measured by titration with 0.2 N hydrochloric acid in isopropanol. After reactor cools down to 65° C. and the pressure get back to atmospheric, nitrogen is bubbled in the mixture for 2 hours before recovering the product.

Example 5: Synthesis of Esterquat GC According to Example M1 of WO 2008/089906 (Comparative Example)

567 g (2.1 moles) of partly hydrogenated palm oil fatty acid, 219 g (1.5 moles) of adipic acid and 0.3 g of hypophosphoric acid (50 wt % aqueous solution) are introduced into a stirred reactor and heated to 70° C. under a reduced pressure of 2 kPa. Triethanolamine (447 g; 3 moles) are then added drop wise in portions and, at the same time, the temperature is raised up to 120° C. After the addition, the reaction mixture is heated to 160° C., the pressure is reduced to 6.67 kPa and the mixture is stirred under those conditions for 2.5 hours, until the acid value falls below 5 mg KOH.g$^{-1}$. The mixture is then cooled to 60° C., the vacuum is broken by introduction of nitrogen, and 0.6 g of hydrogen peroxide is added in the form of a 30 wt % aqueous solution.

For the quaternisation step, the resulting ester was dissolved in 376 g of isopropyl alcohol, and 357 g (2.83 moles) of dimethyl sulphate are added to the resulting solution over a period of 1 hour at such a rate that the temperature does not rise above 65° C.

After the addition, the mixture is stirred for another 2.5 h, the total nitrogen content being regularly checked by sampling. The reaction is terminated when constant total nitrogen content is reached. A product with a solids content of 80 wt % is obtained.

Example 6: Calcium Carbonate Ore Beneficiation

The flotation tests are performed in a 2.8 L plastic bowl with the laboratory flotation cell from Outotec.

800 g of calcium carbonate ore containing 3.3 wt % impurities are mixed with 2.4 L of water in the plastic bowl of the flotation cell. The turbine agitation speed is set up to 1200 rpm to insure a total suspension of the ore in the cell.

Final beneficiation is obtained in two flotation steps run in the same cell one after the other. First step lasts 8 minutes and second step 14 minutes.

Before each step, the slurry is conditioned during 2 minutes with the collector before introducing the air in the cell. The air flow rate is set to 2 L.min$^{-1}$.

During flotation experiment, froth is removed regularly with a plastic spatula and collected for analysis.

The purified carbonate sample is filtrated, weighed after drying and analysed. Hydrochloric acid attack is followed by a second drying and weighing in order to measure the amount of acidic insoluble compounds (remaining silicates). The HCl attack aims at obtaining a complete dissolution of calcium carbonate by an appropriate dissolution with concentrated hydrochloric acid solution (typically 10 wt % in water). The remaining minerals that are not digested correspond to the silicates (impurities).

The froth is also rinsed and filtrated. It is then dried, weighed, submitted to HCl attack, dried and weighed again in order to deduce the amount of impurities and the calcium carbonate losses.

In order to get more significant comparison data, all the collectors are diluted with isopropyl alcohol to get an isopropyl alcohol content of 30 wt % (as determined by Gas Chromatography analysis) before being used in the test.

Results are expressed as calcite ore purity after treatment and loss of ore during treatment. Target is an as high as possible purity with loss as low as possible. Results are considered acceptable if purity is over 99.85 wt % and loss below 5 wt %.

The results of calcite ore beneficiation with collectors A, B and C according to the invention (Examples 1-3) are presented in Table 1 here below:

TABLE 1

| Collector | Dosage (ppm) (1st step/2nd step) | Calcite purity after treatment (wt %) | Calcite loss (wt %) |
|---|---|---|---|
| A | 450 + 100 | 99.98 | 3.2 |
| B | 550 + 150 | 99.90 | 2.9 |
| C | 450 + 150 | 99.93 | 1.9 |

Example 7: Calcium Carbonate Flotation in Harsh Conditions

The flotation tests are performed with the laboratory flotation cell from Outotec.

800 g of calcium carbonate ore containing 2.2 wt % of impurities (HCl insoluble) are mixed with 2.4 L of water in the plastic bowl of the flotation cell. The turbine agitation speed is set up to 1200 rpm to insure a total suspension of the ore in the cell.

Standard flotation test is run at natural pH of the pulp (pH=8.9) and tap water temperature at 19° C. When flotation tests are run in so called "harsh conditions", pH of the slurry is set to 10 using calcium hydroxide and water is heated up to 30° C.

Final beneficiation is obtained in two flotation steps run in the same cell one after the other. First step lasts 8 min and second step 14 min.

Before each step, the slurry is conditioned during 2 minutes with the collector before introducing the air in the cell. The air flow rate is set to 2 L.min$^{-1}$.

During flotation experiment, froth is removed regularly with a plastic spatula and collected for analysis.

The purified carbonate sample is filtrated, weighed after drying and analysed. Hydrochloric acid attack is followed by a second drying and weighing in order to measure the amount of acidic insoluble compounds (remaining silicates). The HCl attack aims at obtaining a complete dissolution of calcium carbonate by an appropriate dissolution with concentrated hydrochloric acid solution (typically 10 wt % in water). The remaining minerals that are not digested correspond to the silicates (impurities).

The froth is also rinsed and filtrated. It is then dried, weighed, submitted to HCl attack, dried and weighed again in order to deduce the amount of impurities and the calcium carbonate losses.

In order to get more significant comparison data, all the collectors are diluted with isopropyl alcohol to get an isopropyl alcohol content of 30 wt % (as determined by Gas Chromatography analysis) before being used in the test.

Results are expressed as impurities removed during treatment and loss of ore during treatment. The target is of course to get an impurity removal as high as possible with loss as low as possible but results are considered acceptable if removal is over 93.2 wt % and loss below 5 wt %.

The results of calcite ore beneficiation in normal and harsh conditions with collector C according to the invention (Examples 3) and comparative collectors FC and GC (Examples 4 and 5) are presented in Table 2 here below:

TABLE 2

| | | Standard conditions | | Harsh conditions | |
|---|---|---|---|---|---|
| Collector | Dosage (1st step/2nd step) | Impurities removed (wt %) | Calcite loss (wt %) | Impurities removed (wt %) | Calcite loss (wt %) |
| C | 420 + 150 ppm | 96.6 | 3.3 | 94.3 | 2.3 |
| FC | 500 + 250 ppm | 94.3 | 4.0 | 67.6 | 1.4 |
| GC | 500 + 250 ppm | 94.9 | 3.2 | 86.4 | 1.9 |

It has to be noticed that, in order to obtain the desired level of impurities removal in standard conditions, collectors according to prior art required an extra 30% dosage compared to the collector according to the invention. Despite this extra dosage, impurity removal drops down quickly in harsh conditions with the prior art collectors while collectors for use in the present invention maintain their activity at a more than acceptable level.

Example 8: Cationic Collector for Phosphate Ore Beneficiation

Phosphate ore sample containing silica impurities is treated by reverse froth flotation. Flotation test is run in the laboratory flotation cell provided by the company Outotec.

340 g of grinded phosphate ore are mixed with 2.5 L of water in the plastic bowl of the flotation cell. The turbine agitation speed is set up to 1500 rpm to insure a total suspension of the ore in the cell.

0.34 g of phosphoric acid (85% grade) are added to the slurry and agitation is maintained for 3 minutes. Then, 0.17 g of a carbonate collector supplied by CECA S.A. under trade name Melioran® P312 is added to the slurry and agitation is maintained for another 2 minutes before air injection starts. Air flow rate is set up to 3 L.min$^{-1}$ and froth is collected manually during 2 minutes before air injection is stopped.

Then, 10.2 g of cationic collector C (Example 3) is added to the slurry and left under agitation during 2 minutes before air injection starts again. Froth is collected manually. Test is stopped after 4 minutes of froth collection.

The ore remaining is the cell is then filtered and dried in an oven overnight.

Dried ore is weighed to determine the quantity recovered and a sample is sent to analysis in order to determine precisely the composition after treatment.

Before reverse froth flotation beneficiation, the ore (fluoro-apatite type) is containing 43 wt % of calcite and 17 wt % of quartz. $P_2O_5$ content is only 13.8 wt %. The test run only concerns quartz removal and an efficiency over 80% is considered satisfying. Complete results are nevertheless given to prove complete compatibility of the whole process and the achievement of the $P_2O_5$ enrichment around 30 wt %, that is a standard target for phosphate ore beneficiation.

The results for collector C are provided in the below Table 3.

TABLE 3

| Collector | Silicate collection (wt %) | Calcite collection (wt %) | $P_2O_5$ content after treatment (wt %) |
|---|---|---|---|
| C | 81.0 | 86.6 | 29.6 |

The following other collectors (Examples 9-19) have also shown good properties for ore beneficiation.

Examples 9-19 of Table 4 below are prepared following the same reaction conditions as in example 1 and are obtained by reacting the following compounds:

TABLE 4

| Example | Alcoxylated fatty amine of formula (I) | dicarboxylic acid or a derivative of formula (II) | Molar ratio (I)/(II) | Alkylating agent for quaternisation reaction |
|---|---|---|---|---|
| 9 | Tallow alkyl amine + 2OE | Adipic acid | 1.33 | Methyl chloride |
| 10 | Tallow alkyl amine + 5OE | Maleic anhydride | 1.33 | Methyl chloride |
| 11 | Tallow alkyl amine + 5OE | Sebacic acid | 1.33 | Methyl chloride |
| 12 | Oleylamine + 5OE | Adipic acid | 1.33 | Methyl chloride |
| 13 | Palm-oil alkyl amine + 5OE | Adipic acid | 1.33 | Methyl chloride |
| 14 | Coco alkyl amine + 2OE | Adipic acid | 1.33 | Methyl chloride |
| 15 | Coco alkyl amine + 5OE | Succinic anhydride | 1.33 | Methyl chloride |
| 16 | Tallow alkyl amine + 2OE | Adipic acid | 1.5 | Methyl chloride |
| 17 | Tallow alkyl amine + 5OE | Adipic acid | 1.5 | Methyl chloride |
| 18 | Tallow alkyl amine + 5OE | Adipic acid | 1.33 | Dimethyl sulphate |
| 19 | Tallow alkyl amine + 5OE | Adipic acid | 1.33 | Diethyl sulphate |
| 20 | Tallow alkyl amine + 5OE | Glutaric acid | 1.33 | Methyl chloride |

In Table 4 above, the number of ethylene oxide (OE) equivalents that have been reacted with the fatty amine are indicated after the "+"sign. All compounds of examples 9-19 are totally quaternised.

The invention claimed is:

1. A method of beneficiating an ore, comprising contacting the ore with at least one compound represented by formula (1):

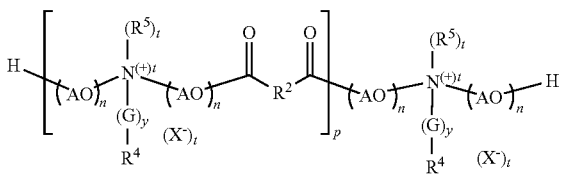

wherein:
$R^2$ is selected from the group consisting of
 a direct bond,
 a $C_1$-$C_{20}$, linear or branched, saturated or unsaturated hydrocarbon chain optionally substituted by one or more —OH group(s), a substituted alkylene radical wherein the alkylene radical is substituted by 1 or 2 —OH groups, an alkenylene radical having from 1-20 carbon atoms, a substituted alkenylene radical, wherein the alkenylene radical is substituted by 1 or 2 methyl and/or methylene groups,
 a cycloalkylene group,
 a cycloalkenylene group, and
 an arylene group;
$R^4$ is a hydrocarbyl group containing 8-24 carbon atoms or a group represented by the formula $R^6$—O-(A'O)$_w$-T-,
 wherein:
  $R^6$ is a hydrocarbyl group containing 8-24 carbon atoms,
  w is an integer ranging from 0 to 20,
  A'O is an alkyleneoxy group containing 2-4 carbon atoms, and
  T is alkylene group containing 1-6 carbon atoms;
$R^5$ is a hydrocarbyl group or a benzyl group;
X is a leaving group selected from halogens, sulphates and carbonates;
AO is an alkyleneoxy group containing 2-4 carbon atoms;
n is an integer of from 1 to 20;
t is 0 or 1;
y is 0 or 1;
p ranges from 1 to 15;
G is a group represented by formula (III):

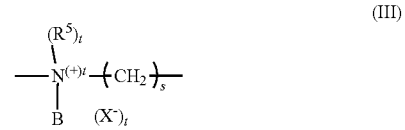

wherein:
 B is an alkyl group containing 1-4 carbon atoms or a benzyl group,
 s is 1, 2 or 3,
 $R^5$, X, and t are as defined above, and
 wherein the group —(CH$_2$)$_s$— is a spacer between the nitrogen atom in formula (III) and the nitrogen atom in formula (1) which is linked to formula (III).

2. The method of claim 1, wherein the at least one compound represented by formula (1) is represented by formula (1A):

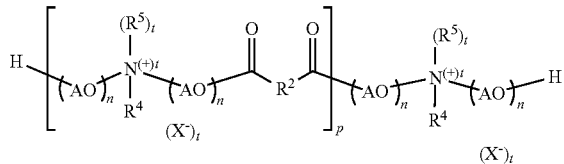

(1A)

wherein AO, n, p, t, $R^2$, $R^4$, $R^5$ and X are as defined in claim 1 and y is 0.

3. The method of claim 2, wherein:
$R^2$ is an alkylene radical represented by the formula —$(CH_2)_z$—, wherein z is an integer from 1 to 20; and
$R^4$ is a hydrocarbyl group having 8-24 carbon atoms.

4. The method of claim 1, wherein:
each t is 1; and
$R^5$ is a methyl or ethyl group.

5. The method of claim 1, wherein:
each n is, independently from one another, 1 to 6; and
p is 1 to 10.

6. The method of claim 1, wherein the ore is selected from the group consisting of calcium carbonates, magnesium carbonates, phosphates, iron ores, and mixtures thereof.

7. The method of claim 1, wherein the ore is selected from the group consisting of calcium carbonates, calcium carbonate-containing materials, and mixtures thereof.

8. The method of claim 1, wherein the ore is selected from the group consisting of wollastonite, barite, titanium oxides, kaolin, kaolinitic clays, calcined kaolinitic clays, montmorillonite, sepiolite, talc, diatomaceous earths, aluminium oxides, sulfates and sulfides, and mixtures thereof.

9. The method of claim 1, wherein the ore is selected from the group consisting of potassium chloride, metal-containing ores, and mixtures thereof, wherein the metal in the metal-containing ores is iron, platinum, aluminium, nickel, copper, or a mixture thereof.

10. The method of claim 1, wherein the content at least one mineral present in in the ore is reduced, where the at least one mineral is selected from the group consisting of graphite, iron sulfides, iron oxides, iron hydroxides, iron oxyhydroxides, silica, silicates, mica, clays, potash, and mixtures thereof.

11. The method of claim 1, wherein the content of the compound represented by formula (1) is from 10 ppm to 5000 ppm by weight relative to the amount of the ore.

12. The method of claim 1, where beneficiating of the ore occurs by direct flotation.

13. The method of claim 1, where beneficiating of the ore occurs by reverse flotation.

14. A flotation pulp, comprising water, ground ore containing impurities, and at least compound represented by formula (1):

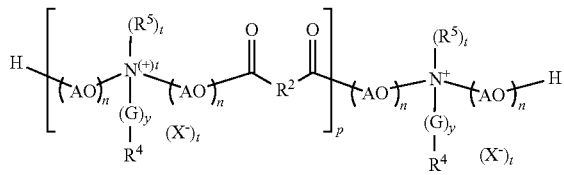

(1)

wherein:
$R^2$ is selected from the group consisting of
a direct bond,
a $C_1$-$C_{20}$, linear or branched, saturated or unsaturated hydrocarbon chain optionally substituted by one or more —OH group(s), a substituted alkylene radical wherein the alkylene radical is substituted by 1 or 2 —OH groups, an alkenylene radical having from 1-20 carbon atoms, a substituted alkenylene radical, wherein the alkenylene radical is substituted by 1 or 2 methyl and/or methylene groups,
a cycloalkylene group,
a cycloalkenylene group, and
an arylene group;
$R^4$ is a hydrocarbyl group containing 8-24 carbon atoms or a group represented by the formula $R^6$—O-$(A'O)_w$-T-,
wherein:
$R^6$ is a hydrocarbyl group containing 8-24 carbon atoms,
w is an integer ranging from 0 to 20,
A'O is an alkyleneoxy group containing 2-4 carbon atoms, and
T is alkylene group containing 1-6 carbon atoms;
$R^5$ is a hydrocarbyl group or a benzyl group;
X is a leaving group selected from halogens, sulphates and carbonates;
AO is an alkyleneoxy group containing 2-4 carbon atoms;
n is an integer of from 1 to 20;
t is 0 or 1;
y is 0 or 1;
p ranges from 1 to 15;
G is a group represented by formula (III):

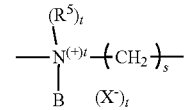

(III)

wherein:
B is an alkyl group containing 1-4 carbon atoms or a benzyl group,
s is 1, 2 or 3,
$R^5$, X, and t are as defined above, and
wherein the group —$(CH_2)_s$— is a spacer between the nitrogen atom in formula (III) and the nitrogen atom in formula (1) which is linked to formula (III).

15. The flotation pulp of claim 14, having at least one of the following characteristics:
a solid weight content of the pulp of from 5 wt % to 50 wt %, and
a content of the at least one compound represented by formula (1) of from 0.001 wt % to 0.5 wt % based on the solids weight content of the pulp.

16. Tailings comprising floated impurities and at least one compound represented by formula (1):

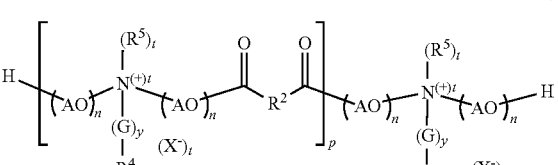

(1)

wherein:
R² is selected from the group consisting of
a direct bond,
a $C_1$-$C_{20}$, linear or branched, saturated or unsaturated hydrocarbon chain optionally substituted by one or more —OH group(s), a substituted alkylene radical wherein the alkylene radical is substituted by 1 or 2 —OH groups, an alkenylene radical having from 1-20 carbon atoms, a substituted alkenylene radical, wherein the alkenylene radical is substituted by 1 or 2 methyl and/or methylene groups,
a cycloalkylene group,
a cycloalkenylene group, and
an arylene group;
R⁴ is a hydrocarbyl group containing 8-24 carbon atoms or a group represented by the formula $R^6$—O-$(A'O)_w$-T-,
wherein:
R⁶ is a hydrocarbyl group containing 8-24 carbon atoms,
w is an integer ranging from 0 to 20,
A'O is an alkyleneoxy group containing 2-4 carbon atoms, and
T is alkylene group containing 1-6 carbon atoms;
R⁵ is a hydrocarbyl group or a benzyl group;
X is a leaving group selected from halogens, sulphates and carbonates;
AO is an alkyleneoxy group containing 2-4 carbon atoms;
n is an integer of from 1 to 20;
t is 0 or 1;
y is 0 or 1;
p ranges from 1 to 15;
G is a group represented by formula (III):

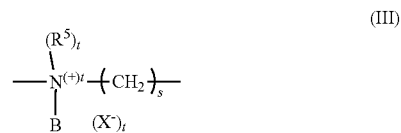

wherein:
B is an alkyl group containing 1-4 carbon atoms or a benzyl group,
s is 1, 2 or 3,
R⁵, X, and t are as defined above, and
wherein the group —$(CH_2)_s$— is a spacer between the nitrogen atom in formula (III) and the nitrogen atom in formula (1) which it-is linked to formula (III).

17. The tailings of claim 16, comprising, relative to the total weight of the tailings when dried, from 50 wt % to 99.995 wt % of floated impurities and from 0.005 wt % to 35 wt % of the at least one compound represented by formula (1).

* * * * *